US00PP16881P2

(12) United States Plant Patent
Kobayashi

(10) Patent No.: US PP16,881 P2
(45) Date of Patent: Jul. 25, 2006

(54) POINSETTIA PLANT NAMED 'PER1056'

(50) Latin Name: *Euphorbia pulcherrima*
Varietal Denomination: PER1056

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 11/151,840

(22) Filed: Jun. 14, 2005

(51) Int. Cl.
*A01H 5/00* (2006.01)

(52) U.S. Cl. ..... Plt./307

(58) Field of Classification Search ..... Plt./307
See application file for complete search history.

*Primary Examiner*—Kent Bell
(74) *Attorney, Agent, or Firm*—C. A. Whealy

(57) ABSTRACT

A new and distinct cultivar of Poinsettia plant named 'PER1056', characterized by its uniform, upright and mounded plant habit; vigorous growth habit; dark green-colored leaves; inflorescences with dark crimson red-colored flower bracts; early-season flowering; and excellent post-production longevity.

1 Drawing Sheet

Botanical designation: *Euphorbia pulcherrima* Willd.
Cultivar denomination: 'PER1056'.

BACKGROUND OF THE INVENTION

The present Invention relates to a new and distinct cultivar of Poinsettia plant, botanically known as *Euphorbia pulcherrima* Willd., and hereinafter referred to by the name 'PER1056'.

The new Poinsettia a product of a planned breeding program conducted by the Inventor in Encinitas, Calif. The objective of the breeding program is to create new early flowering Poinsettia cultivars having strong stems, recurved leaves and flower bracts, attractive flower bract coloration, uniform plant habit and excellent post-production longevity.

The new Poinsettia originated from a cross-pollination made by the Inventor in December, 1999, of a proprietary selection of *Euphorbia pulcherrima* Willd. identified as code number V-47, not patented, as the female, or seed, parent, with the *Euphorbia pulcherrima* cultivar 490, disclosed in U.S. Plant Pat. No. 7,825, as the male, or pollen, parent. The cultivar PER1056 was discovered and selected by the Inventor as a flowering plant within the progeny of the stated cross-pollination in a controlled environment in Encinitas, Calif., in November, 2000.

Asexual reproduction of the new Poinsettia by terminal cuttings propagated in a controlled environment in Encin itas, Calif., since January, 2001, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'PER1056'. These characteristics in combination distinguish 'PER1056' as a new and distinct cultivar:

1. Uniform, upright and mounded plant habit.
2. Vigorous growth habit.
3. Dark green-colored leaves.

4. Inflorescences with dark crimson red-colored flower bracts.
5. Early-season flowering; natural season flower maturity date is late November for plants grown in Encinitas, Calif.
6. Excellent post-production longevity.

Plants of the new Poinsettia differ from plants of the female parent selection primarily in the following characteristics:

1. Plants of the new Poinsettia have darker green-colored leaves than plants of the female parent selection.
2. Plants of the new Poinsettia flower about 10 days earlier than plants of the female parent selection.
3. Plants of the new Poinsettia have darker red-colored flower bracts than plants of the female parent selection.

Plants of the new Poinsettia differ from plants of the male parent, the cultivar 490, primarily in flower time as plants of the new Poinsettia flower later than plants of the cultivar 490.

Plants of the new Poinsettia can be compared to plants of the cultivar Peterstar, disclosed in U.S. Plant Pat. No. 8,259. In side-by-side comparisons conducted in Encinitas, Calif., plants of the new Poinsettia differed from plants of the cultivar Peterstar in the following characteristics:

1. Plants of the new Poinsettia had darker green-colored leaves than plants of the cultivar Peterstar.
2. Plants of the new Poinsettia had darker red-colored flower bracts than plants of the cultivar Peterstar.
3. Plants of the new Poinsettia flowered about five days earlier than plants of the cultivar Peterstar.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the colors of the new Poinsettia.

The photograph at the bottom of the sheet comprises a side perspective view of a typical flowering plant of 'PER1056' grown in a container.

The photograph at the top of the sheet is a close-up view of typical inflorescences of 'PER1056'.

DETAILED BOTANICAL DESCRIPTION

The new Poinsettia has not been observed under all possible environmental conditions. The phenotype may vary somewhat with variations in environment such as termperature, daylength and light intensity, without, however, any variance in genotype.

The aforementioned photographs, following observations and averaged measurements describe plants grown in Encinitas, Calif. during the spring under commercial practice in a polyethylene-covered greenhouse with day temperatures averaging about 24° C., night temperatures averaging about 19° C. and light levels about 4,000 foot-candles. Single plants were grown in 16.5-cm pots and pinched once. Plants were flowered under natural season short day/long night conditions. Plants were about 14 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar PER1056.

Parentage:

*Female parent*.—Proprietary selection of *Euphorbia pulcherrima* Willd. identified as code number V-47, not patented.

*Male parent*.—*Euphorbia pulcherrima* Willd. cultivar 490, disclosed in U.S. Plant Pat. No. 7,825.

Propagation:

*Type cutting*.—Terminal cuttings.

*Time to initiate roots*.—About 10 days at 20 to 22° C.

*Time to develop roots*.—About four weeks at 20 to 22° C.

*Root description*.—Thick, fibrous; white in color.

*Rooting habit*.—Freely branching.

Plant description:

*Growth habit*.—Upright, uniform and mounded plant habit; inverted triangle. Vigorous growth habit.

*Plant height*.—About 27 cm.

*Plant diameter or spread*.—About 39 cm.

*Lateral branch description*.—Quantity: About eight lateral branches develop after pinching. Length: About 20 cm. Diameter: About 6 mm. Internode length: About 2.5 cm. Strength: Strong. Texture: Smooth; glabrous. Color: 146A.

*Foliage description*.—Arrangement: Alternate, single. Length: About 12.6 cm. Width: About 10 cm. Shape: Elliptic. Apex: Acuminate. Base: Acute. Margin: Entire with irregular lobing. Venation pattern: Pinnate. Texture, upper surface: Glabrous, smooth. Texture, lower surface: Slightly pubescent. Color: Developing foliage, upper surface: 147A. Developing foliage, lower surface: 147B. Fully expanded foliage, upper surface: Darker than 147A. Fully expanded foliage, lower surface: 147B. Venation, upper surface: 146A. Venation, lower surface: 147C. Petiole: Length: About 6.7 cm. Diameter: About 3 mm. Texture, upper and lower surfaces: Smooth; glabrous. Color, upper and lower surfaces: 185A.

Inflorescence description:

*Inflorescence type and habit*.—Inflorescences are compound corymbs of cyathia with colored flower bracts subtending the cyathia. One inflorescence per lateral branch. Flowers are not fragrant. Flowers persistent.

*Natural flowering season*.—Autumn/winter in Northern Hemisphere. Flower initiation and development is induced under long nyctoperiod conditions. Early season flowering, response time, about 8 weeks; natural season flower maturity date is late November for plants grown in Encinitas, Calif.

*Post-production longevity*.—Plants of the new Poinsettia maintain good substance and bract color for about four weeks under interior conditions.

*Inflorescence size*.—Diameter: About 28 cm. Height (depth): About 2.8 cm.

*Flower bracts*.—Quantity per inflorescence: About 18. Length, largest bracts: About 13.5 cm. Width, largest bracts: About 10.5 cm. Shape: Elliptic. Apex: Acuminate. Base: Acute. Margin: Entire with occasional lobing. Texture, upper and lower surfaces: Glabrous; velvety. Surface, upper and lower surfaces: Smooth. Aspect: Mostly flat. Venation pattern: Pinnate. Color: Developing and transitional bracts, upper surface: 46A. Developing and transitional bracts, lower surface: 53B. Fully expanded bracts, upper surface: Brighter than 53B. Fully expanded bracts, lower surface: 53B. Venation, upper and lower surfaces: Similar to flower bract color. Bract petiole: Length: About 2.4 cm. Diameter: About 2 mm. Texture, upper and lower surfaces: Smooth; glabrous. Color, upper and lower surfaces: 185A.

*Cyathia*.—Quantity per corymb: About ten. Diameter of cyathia cluster: About 2 cm. Length: About 1 cm. Width: About 6 mm. Shape: Ovoid. Color, immature: 146B. Color, mature: 146B to 146C. Nectaries: Quantity per cyathium: About one or two. Size: About 3 mm by 4 mm. Color: 15A. Peduncle: Length: About 4 mm. Diameter: About 2 mm. Strength: Strong. Aspect: Mostly upright. Texture: Smooth; glabrous. Color: 145A. Stamens: Quantity per cyathium: About ten. Anther shape: Bi-lobed. Anther length: Less than 1 mm. Anther color: 185A. Amount of pollen: Scarce. Pollen color: 12A. Pistils: None observed.

Disease/pest resistance: Resistance to pathogens and pests common to Poinsettias has not been observed on plants grown under commercial conditions.

It is claimed:

1. A new and distinct cultivar of Poinsettia plant named 'PER1056', as illustrated and described.

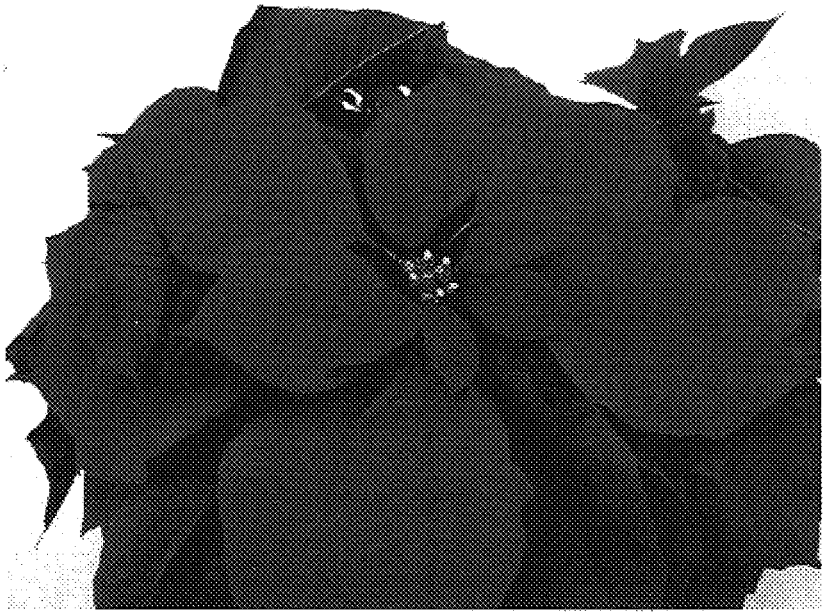
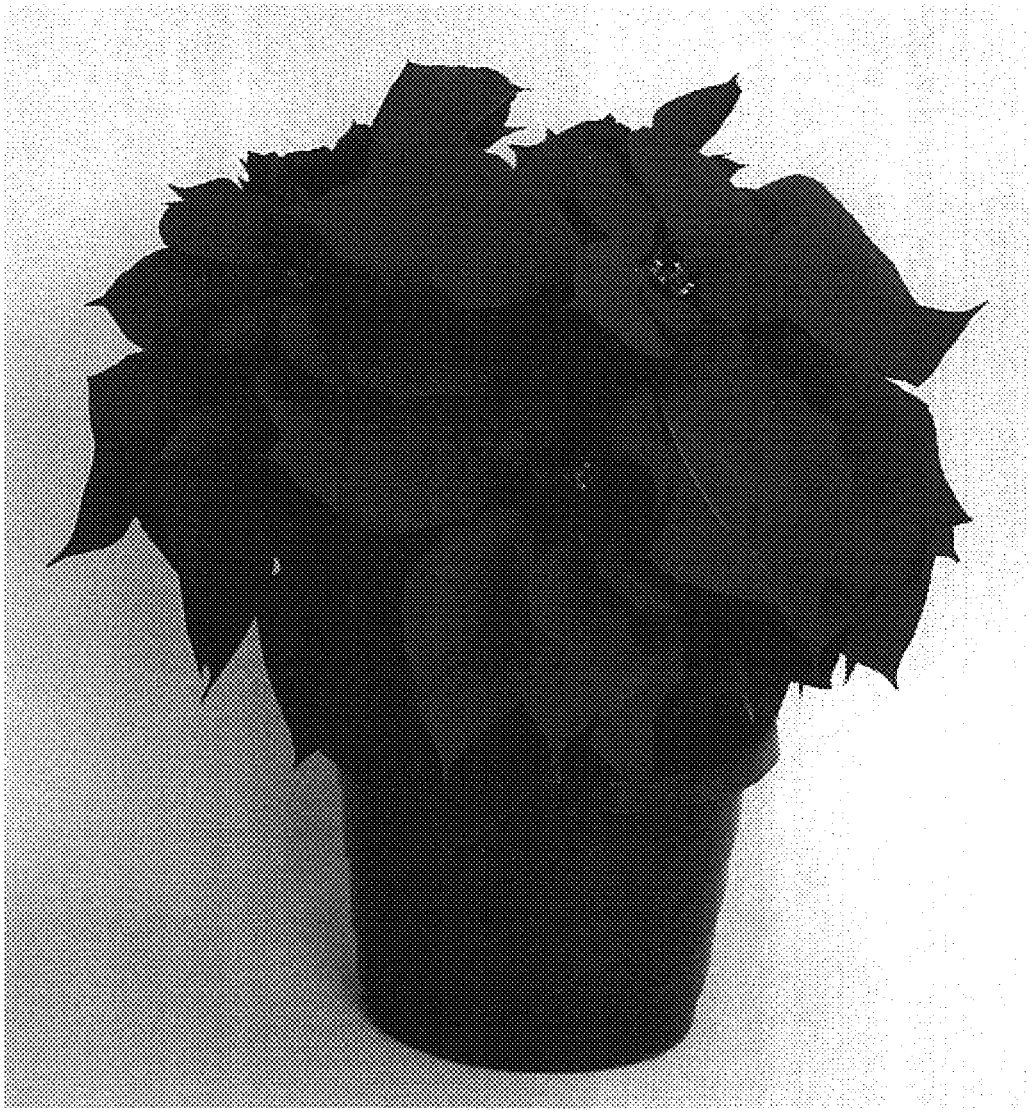

* * * * *